United States Patent
Lee

(10) Patent No.: US 11,946,027 B2
(45) Date of Patent: Apr. 2, 2024

(54) SYSTEMS AND METHODS FOR MONITORING BEHAVIOR OF CELLS AND/OR TISSUES IN CULTURING MEDIA

(71) Applicant: Purdue Research Foundation, West Lafayette, IN (US)

(72) Inventor: Chi-Hwan Lee, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 602 days.

(21) Appl. No.: 16/883,427

(22) Filed: May 26, 2020

(65) Prior Publication Data

US 2020/0370000 A1     Nov. 26, 2020

Related U.S. Application Data

(60) Provisional application No. 62/852,865, filed on May 24, 2019.

(51) Int. Cl.
    *C12M 1/34*       (2006.01)
    *C12M 1/09*       (2006.01)
    (Continued)

(52) U.S. Cl.
    CPC .......... *C12M 1/3407* (2013.01); *C12M 21/08* (2013.01); *C12M 23/56* (2013.01);
    (Continued)

(58) Field of Classification Search
    None
    See application file for complete search history.

(56) References Cited

U.S. PATENT DOCUMENTS

| 2007/0207186 A1* | 9/2007 | Scanlon ................. B29C 55/26 623/1.42 |
| 2016/0032074 A1* | 2/2016 | Aizenberg .............. A61L 29/16 427/372.2 |

(Continued)

OTHER PUBLICATIONS

Lei. "Evaluation of Encapsulated IPMC Sensor Based on Thick Parylene Coating." Proceedings of the ASME 2012 Conference on Smart Materials, Adaptive Structures and Intelligent Systems. vol. 1. 2013. https://doi.org/10.1115/SMASIS2012-7975 (Year: 2013).*

(Continued)

*Primary Examiner* — Holly Kipouros
*Assistant Examiner* — Nathan G Esperon
(74) *Attorney, Agent, or Firm* — Hartman Global IP Law; Gary M. Hartman; Domenica N. S. Hartman

(57) ABSTRACT

Systems and methods for monitoring and tracking the behavior of cells and tissues in a culturing medium, for example, in a cell culture medium or an in vivo tissue environment, using a tissue scaffold system having one or more sensor arrays. Such monitoring systems include a tissue scaffold system and one or more sensor arrays on the tissue scaffold system in vertically stackable configurations. The sensor array(s) are configured to monitor electrical impedance and/or electrophysiological activities of cells or tissues which may be provided to an external data acquisition system for production of a three-dimensional (3D) map.

20 Claims, 13 Drawing Sheets
(12 of 13 Drawing Sheet(s) Filed in Color)

(51) Int. Cl.
  C12M 1/12    (2006.01)
  C12M 3/00    (2006.01)
  C12N 5/00    (2006.01)
  G01N 33/483  (2006.01)

(52) U.S. Cl.
  CPC ....... *C12N 5/0068* (2013.01); *G01N 33/4836* (2013.01); *C12M 25/14* (2013.01); *C12N 2513/00* (2013.01)

(56) References Cited

U.S. PATENT DOCUMENTS

2017/0051111 A1* 2/2017 Duan ................ C08G 73/125
2019/0133752 A1* 5/2019 Kaplan ................ A61F 2/142

OTHER PUBLICATIONS

Myllymaa. Surface characterization and in vitro biocompatibility assessment of photosensitive polyimide films. Colloids and Surfaces B: Biointerfaces. vol. 76, Issue 2. 2010. pp. 505-511. https://doi.org/10.1016/j.colsurfb.2009.12.011. (Year: 2010).*
PolymersNetBase ("PTFE"). Downloaded Feb. 9, 2023 (Year: 2023).*
Dai, X., Zhou, W., Gao, T. et al. Three-dimensional mapping and regulation of action potential propagation in nanoelectronics-innervated tissues. Nature Nanotech 11, 776-782 (2016). https://doi.org/10.1038/nnano.2016.96 (Year: 2016).*
Xu "Materials and Fractal Designs for 3D Multifunctional Integumentary Membranes with Capabilities in Cardiac Electrotherapy." Adv. Mater. 27, 1731-1737 (Year: 2015).*
Dai, "Mesh Nanoelectronics: Seamless Integration of Electronics with Tissues" Accounts of Chemical Research 2018 51 (2), 309-318 DOI: 10.1021/acs.accounts.7b00547 (Year: 2018).*
MicroChem "SU-8 2000" Downloaded Feb. 8, 2023 (Year: 2023).*
Lee, S., Sasaki, D., Kim, D. et al. Ultrasoft electronics to monitor dynamically pulsing cardiomyocytes. Nature Nanotech 14, 156-160 (2019). https://doi.org/10.1038/s41565-018-0331-8 (Year: 2018).*
Feiner, R. et al., "Engineered hybrid cardiac patches with multi-functional electronics for online monitoring and regulation of tissue function", Nature Materials | vol. 15 | Jun. 2016 | www.nature.com/naturematerials, (8 pgs).
Fu, T.M. et al., "Highly scalable multichannel mesh electronics for stable chronic brain electrophysiology", PNAS | Published online Nov. 6, 2017, (pp. E10046-E10055).
Tian, B. et al., "Macroporous nanowire nanoelectronic scaffolds for synthetic tissues", Nature Materials j vol. 11 Nov. 2012 j www.nature.com/naturematerials, (pp. 986-994).
Zhou, T. et al., "Syringe-injectable mesh electronics integrate seamlessly with minimal chronic immune response in the brain", PNAS | Jun. 6, 2017 | vol. 114 | No. 23, (pp. 5894-5899).

* cited by examiner

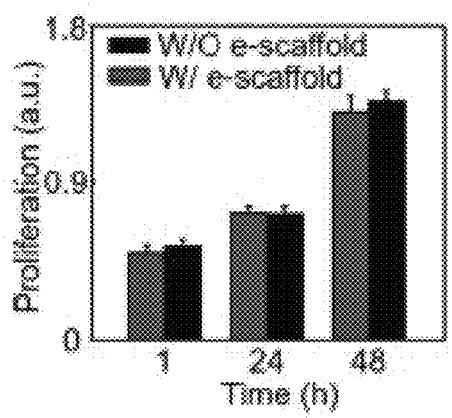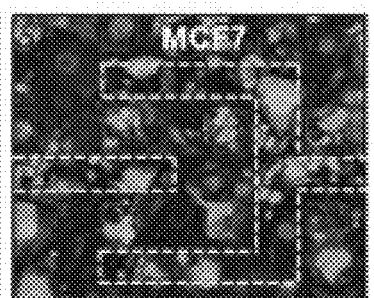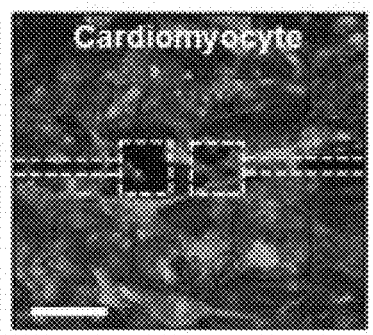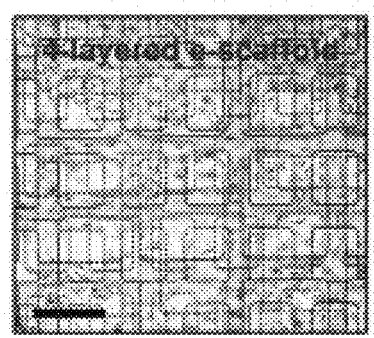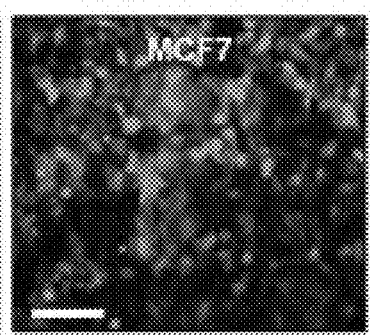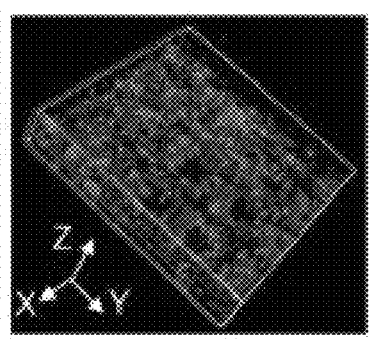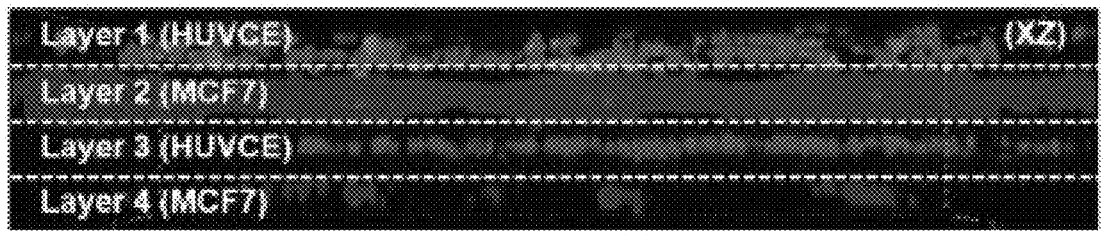

FIG. 3A
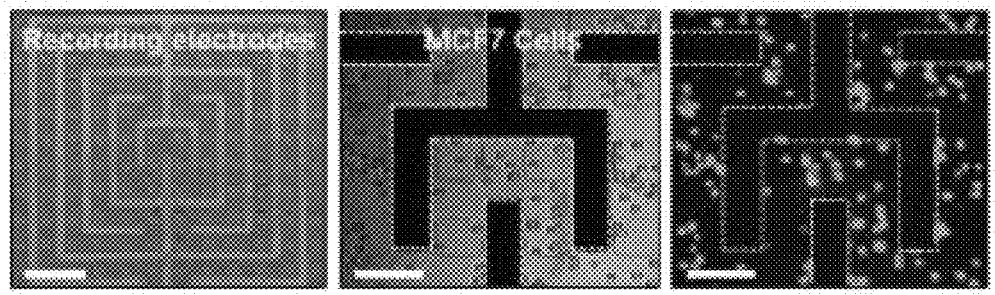
FIG. 3B 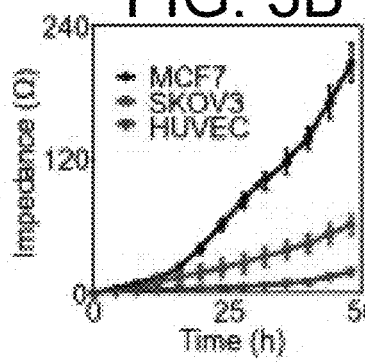 FIG. 3C 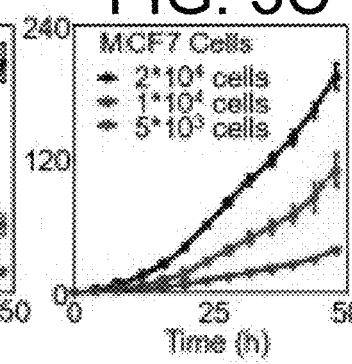 FIG. 3D 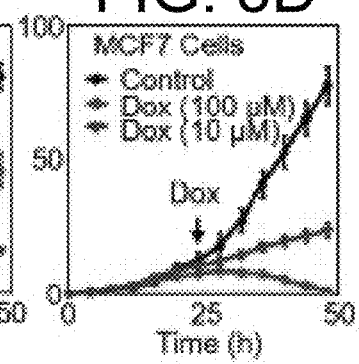
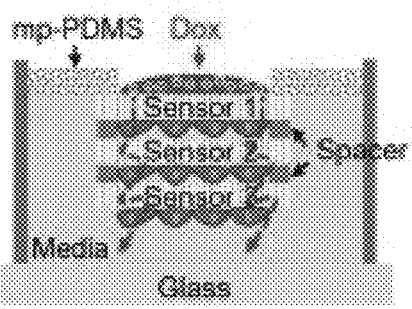
FIG. 3E
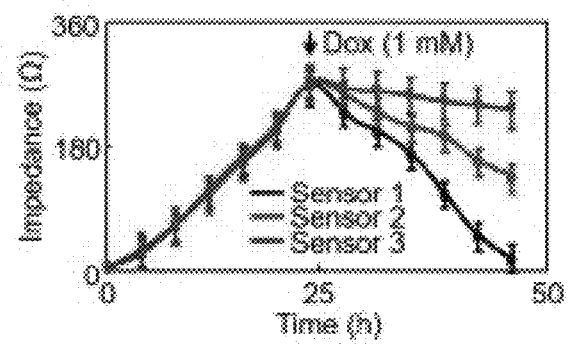
FIG. 3F Layer 1 HUVEC (DRAQ5/GFP)
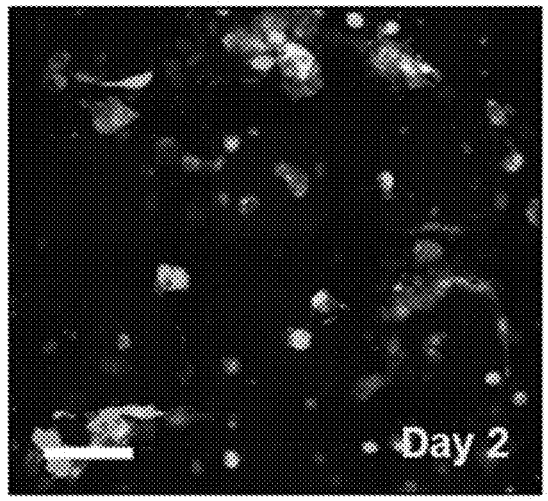
Layer 2 MCF7 (Hoechst/GFP)
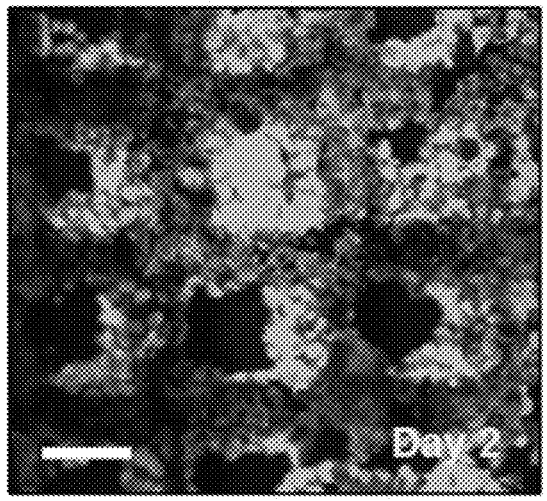
Layer 3 HUVEC (DRAQ5/GFP)
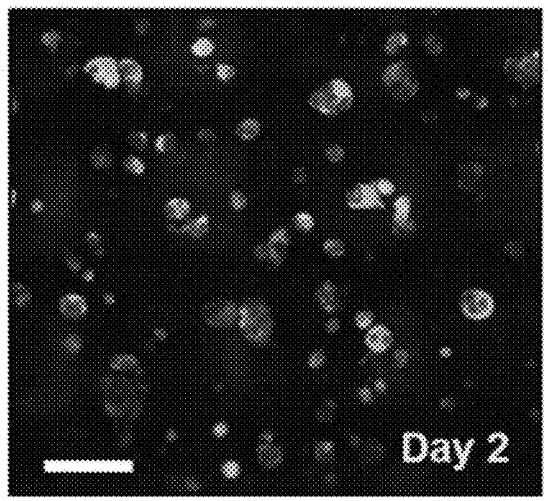
Layer 4 MCF7 (Hoechst/GFP)
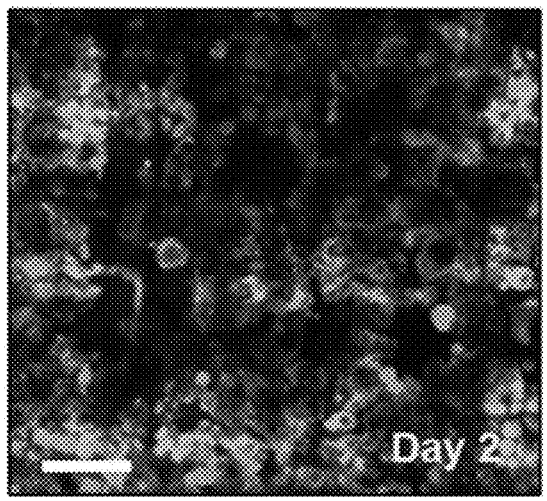
FIG. 7

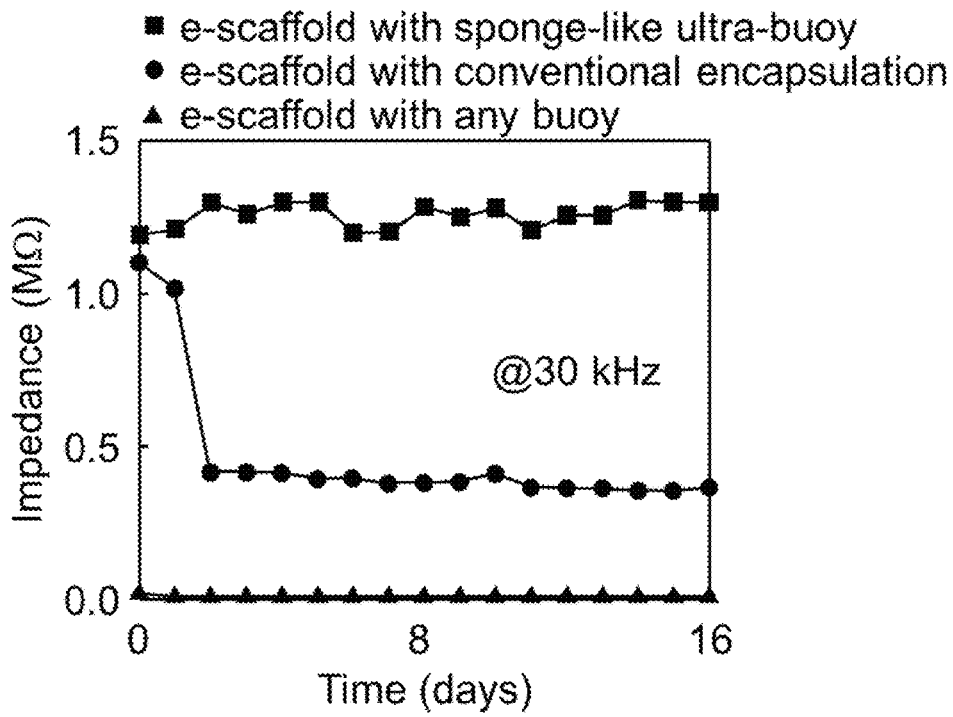

FIG. 12

Table S1. Summary of the experimental results for the ultrahydrophobicity, water-resistance, static immersion, and effective specific weight of the sponge-like PDMS.

| | Cell Medium Contact Angle | Critical Immersion Depth (mm) | Critical Immersion Mass (g) | Surface Pressure (N/m$^2$) | Boyancy Pressure (N/m$^2$) | Density (kg/m$^3$) |
|---|---|---|---|---|---|---|
| PDMS | 102.0°±2.6° | -3.4 | 7.6 | 1.4±0.3 | 36.4 | 965 |
| Sponge-like PDMS | 128.7°±4.9° | -4.0 | 8.1 | 3.7±0.3 | 42.4 | 456 |
| Sponge-like PDMS w/Teflon | 137.2°±3.3° | -4.5 | 8.3 | 4.3±0.2 | 46.7 | 456 |
| Sponge-like PDMS w/Teflon & NPs | 151.4°±1.8° | -4.9 | 8.8 | 5.1±0.1 | 51.2 | 456 |

FIG. 13

SYSTEMS AND METHODS FOR MONITORING BEHAVIOR OF CELLS AND/OR TISSUES IN CULTURING MEDIA

CROSS-REFERENCE TO RELATED APPLICATIONS

This application claims the benefit of U.S. Provisional Application No. 62/852,865 filed May 24, 2019, the contents of which are incorporated herein by reference.

STATEMENT REGARDING FEDERALLY SPONSORED RESEARCH

This invention was made with government support under FA2386-16-1-4105 awarded by the Air Force Office of Scientific Research and FA2386-18-1-4071 awarded by the Air Force Office of Scientific Research. The government has certain rights in the invention.

BACKGROUND OF THE INVENTION

The present invention generally relates to systems for monitoring cellular and tissue behavior. The invention particularly relates to a three-dimensional (3D) mapping system suitable for monitoring and tracking the behavior of cells and tissues in culturing media.

Often following diagnosis and treatment for cancer and other diseases, patients' organs and cells can remain damaged from the treated medical condition. In fact, one of the fastest growing medical markets is healing and/or replacing organs and cells already treated, yet which remain damaged by cancer, cardiovascular disease, or other medical issues. A particular challenge is how to monitor and continuously test the performance of engineered tissues and cells to replace those that have been damaged.

The ability to record cellular and tissue behaviors and functions with high spatial and temporal resolutions enables a fundamental understanding of the underlying biophysics and cellular electrophysiology. Notable existing approaches involve utilizing a variety of recording instrumentations, including optical imagers with voltage-sensitive dyes, graphene-based sensors, multiplexed electrode arrays, and planar field-effect transistors (FETs). However, spatial resolution remains limited because these methods are tailored for two-dimensional (2D) cultured cells. Recent advent of injectable or rollable scaffold systems enables the spatially-resolved three-dimensional (3D) mapping of cellular behaviors and functions in human tissue-mimicking environments. Nonetheless, challenges remain for their long-term, high-fidelity recording due to a lack of effective means to electrically decouple all the necessary electronic instrument settings from the submerged condition in a cell culture medium, including oxygen, pH, conductivity, and/or agitation, which often requires additional packaging to prevent wetting and damaging In view of the above, there is an ongoing desire for systems and methods for monitoring and tracking cellular and tissue behavior and functions in real time.

BRIEF DESCRIPTION OF THE INVENTION

The present invention provides systems and methods suitable for monitoring and tracking the behavior of cells and/or tissues in a culturing medium, for example, in a cell culture medium or an in vivo tissue environment, using a tissue scaffold system having one or more sensor arrays.

According to one aspect of the invention, such a monitoring system includes a tissue scaffold system and one or more sensor arrays on the tissue scaffold system in vertically stackable configurations. The sensor array(s) are configured to monitor electrical impedance and/or electrophysiological activities of cells or tissues which may be provided to an external data acquisition system for production of a three-dimensional (3D) map.

According to another aspect of the invention, such a tissue scaffold system is a buoyant instrumented tissue scaffold system for sensing behaviors and/or functions of cells or tissues in a culturing medium. The scaffold system includes at least one scaffold supported on a buoyant member. The scaffold comprises one or more sensor arrays on one or more flexible member(s). The sensor array(s) are configured to sense the behaviors and/or functions of the cells or tissues in the culturing medium. The system further includes means functionally coupled to the sensor array(s) for transmitting information obtained thereby to an external data acquisition unit. The buoyant member maintains the scaffold and the transmitting means afloat on a surface of the culturing medium, enables the cells to reside and grow beneath the scaffold, and is a barrier to wetting of the sensor array(s) by the culturing medium.

Another aspect of the invention is a method of using the buoyant instrumented tissue scaffold system to sense behaviors and/or functions of cells or tissues in a culturing medium. The method includes locating the scaffold on the culturing medium such that the buoyant member floats on or in the culturing medium and is a barrier to wetting of the sensor array(s) by the culturing medium, allowing the cells or tissues to reside and/or grow beneath the scaffold, detecting the behaviors and/or functions of the cells or tissues with the sensor array(s), and transmitting data to the external data acquisition unit corresponding to the behaviors and/or functions.

Technical effects of systems and methods as described above preferably include the ability to monitor and continuously test the performance of tissues and cells engineered to replace damaged cells and tissues in a patient, for example, whose cells or tissue have been damaged from a disease or treatments of a disease, and/or to monitor cell and tissue functions after surgical transplantation of such engineered cells or tissue in a patient.

Other aspects and advantages of this invention will be appreciated from the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A is an exploded schematic view (left) and an optical image (right) of the scaffold system afloat on a cell culture medium. Scale bar is 1 cm. FIG. 1B includes results of buoyancy and surface tension forces of the scaffold system. FIG. 1C shows sequential optical images of a sponge-like PDMS buoyant member coated with TEFLON® and nanoparticle floating on the cell culture medium against intentional force. Scale bar is 3 cm. FIG. 1D includes SEM images of the sponge-like PDMS buoyant member. All scale bars are 40 μm.

FIGS. 2A-2G include images representing cell compatibility and 3D construction. FIG. 2A shows results of MTT assays for GFP-MCF7 cells seeded on the scaffold system. FIG. 2B is a conformal fluorescence microscope image of a monolayer of the GFP-MCF7 cells at the 2-day incubation (green=GFP, blue=DAPI). Scale bar is 100 μm. FIG. 2C shows results of control experiments with green immunofluorescence stained cardiomyocyte cells at the 8-day incubation (green=FITC, red=Draq5). Scale bar is 60 μm. FIG. 2D is an optical image of a four-layer stacked scaffold system surrounding with dense cell (MCF7) layers after a 3-day incubation. Scale bar is 200 μm. FIG. 2E is a confocal fluorescence microscope image of the stacked scaffold system (green=GFP). Scale bar is 200 μm. FIGS. 2F and 2G include tilted and side views of the stacked scaffold system with alternatively stacked GFP-MCF7 cells and GFP-HUVEC cells (blue=DAPI, red=Draq5).

FIGS. 3A-3F represent real-time multiple monitoring of cellular electrical impedance. FIG. 3A includes representative SEM (left), microscopy (middle), and conformal microcopy (right) images of the scaffold system embedded with impedance sensors (green=GFP). Scale bars are 300 μm, 100 μm, and 100 μm from the left. FIG. 3B shows results of time-dependent impedance for MCF7 cells (black line), SKOV3 cells (red line) and HUVEC cells (green line) for 50 hrs. FIG. 3C shows corresponding results of the different density of the MCF7 cells. FIG. 3D is an impedimetric cytotoxicity plot for the MCF7 cells with Dox. FIG. 3E schematically represents a three-stacked scaffold system within a single Matrigel™ seeded with MCF7 cells. FIG. 3F shows results of real-time multiple monitoring of impedance obtained from the stacked scaffolds. Data are presented as means±S.E. (n=3).

FIG. 4A shows results of ECG signals recorded from the cardiomyocyte at 2, 6, and 8 DIV. FIG. 4B shows continuously recorded ECG signals recorded from the cardiomyocyte at 8 DIV in response to the addition of 100 μL of norepinephrine (NE) into the culture medium. FIG. 4C is a representative microscopy image of an embedded four-channel-multiplexed ECG sensors with cardiomyocytes at 8 DIV. Scale bar is 200 μm. FIG. 4D shows results for synchronized beating of the cardiomyocytes at 8 DIV. FIG. 4E shows results of 3D mapping of action potentials obtained from the total 48 ECG sensors at 2, 6, and 8 DIV.

FIG. 7 includes confocal fluorescence microscope images of the GFP-MCF7 and the GFP-HUVEC cells seeded on the four-layer stacked scaffold system (green=GFP, red=Draq5 and blue=DAPI). Scale bar is 200 μm.

FIG. 12 is a graph plotting electrical impedance versus time for experimental scaffold systems.

FIG. 13 contains Table S1, which represents a summary of experimental results for ultrahydrophobicity, water-resistance, and static immersion of the sponge-like PDMS buoyant member.

DETAILED DESCRIPTION OF THE INVENTION

Disclosed herein is a three-dimensional (3D) mapping system suitable for monitoring and tracking the behavior of the engineered cells and tissues and improving the success rate for patients who have already faced a debilitating disease, for example after surgical transplants in diseased or damaged bodies. The system includes one or more tissue scaffolds with sensor arrays in a stackable configuration that can monitor electrical impedance and/or electrophysiological activities of cells and tissues. The system uses information obtained from the sensor arrays to produce 3D maps to track activity.

Figure 1A:
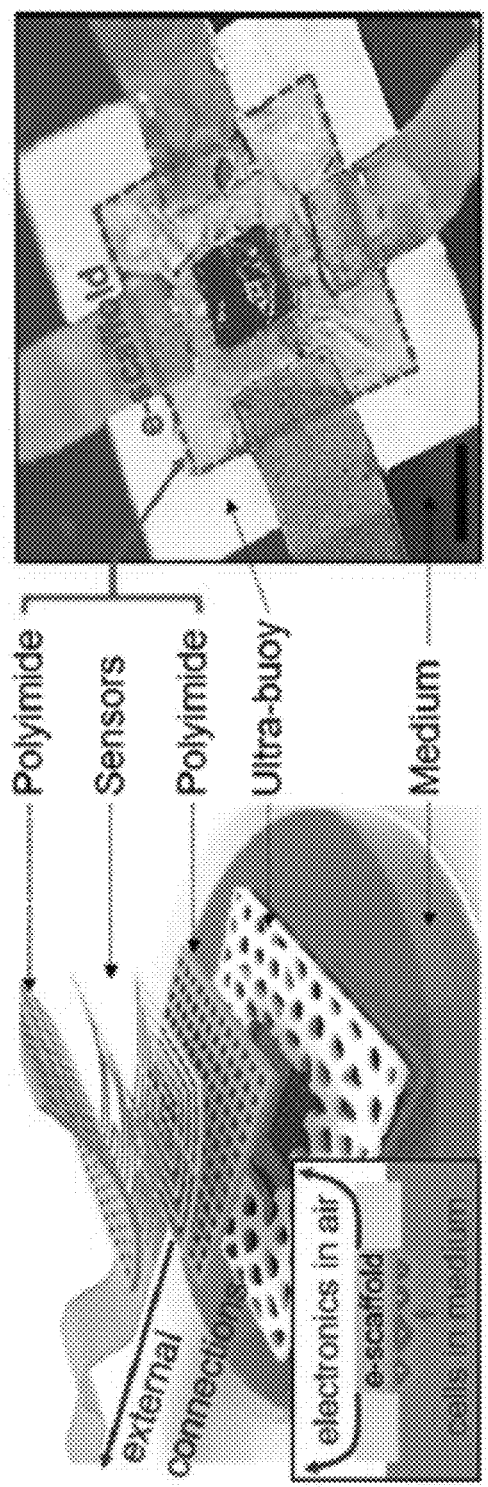
FIGS. 1A-1D include images schematically representing a nonlimiting embodiment of a buoyant instrumented tissue scaffold system.

FIG. 1A shows an exploded schematic view (left image) and an optical image (right image) of a nonlimiting embodiment of a buoyant instrumented tissue scaffold system afloat on a cell culture medium ("Medium"). The basic components of the scaffold system include a buoyant member ("Ultra-Buoy"), and at least one scaffold ("e-scaffold") supported on the buoyant member. The scaffold comprises one or more flexible members ("Polyimide") and one or more sensor arrays ("Sensors") on the flexible member(s). The sensor array(s) are configured to sense the detect electrical cell-substrate impedance and/or electrophysiological signals of cells or tissues in the culture medium. The scaffold system further includes means functionally coupled to the sensor array(s) for transmitting information obtained thereby to an external data acquisition unit. Nonlimiting examples of these components include arrays of multimodal sensors adapted to detect cellular electrical impedance and/or electrophysiological signals, flexible members in the form of thin waterproof elastomeric films (e.g., polyimide films of less than 1 μm thick) to serve as substrate and encapsulation layers, flexible conductors such as anisotropic conductive film (ACF) cables to connect the sensors of the scaffold system to an external data acquisition system, and a buoyant member in the form of a sheet of highly water-repellent ultra-buoyant microporous sponge-like polydimethylsiloxane (sponge-like PDMS) whose effective specific weight is lower than that of the cell culture, for example, at least four times lower, such as about 456 kg/m$^3$ as compared to a cell culture medium of about 1,926 kg/m$^3$. The buoyant member is shown as anchored to the peripheral area of the scaffold(s). A matrix, as a nonlimiting example, a high concentration of cold Matrigel™ (20 mg/ml; Corning Life Sciences), surrounds the scaffold and is capable of containing biological cells. In this configuration, all the electronic components including the flexible conductors remain on the top of the buoyant member to avoid wetting, while cells can reside and grow underneath the scaffold in submerged culture conditions.

Figure 1C:
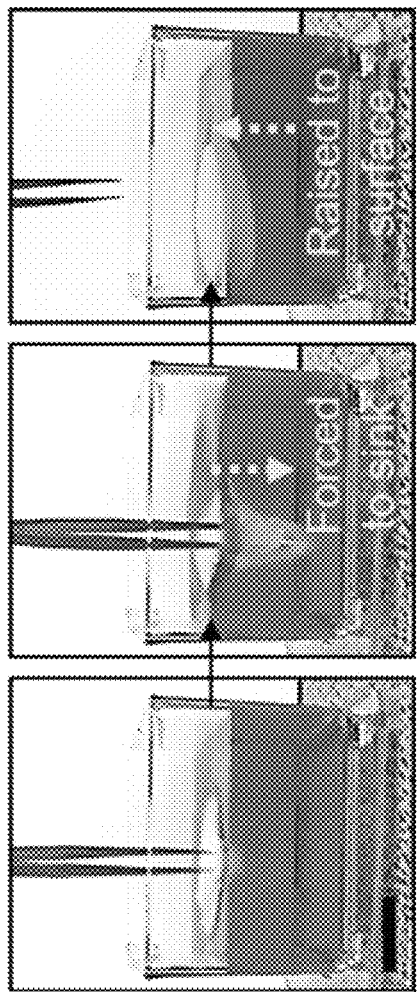
Figure 1B:
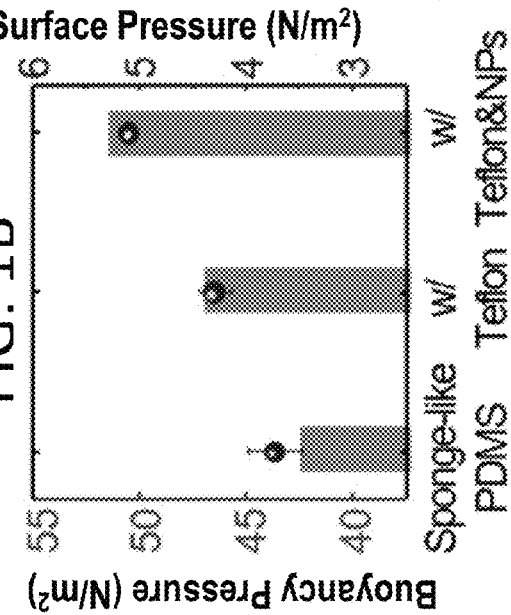
Figure 1D:
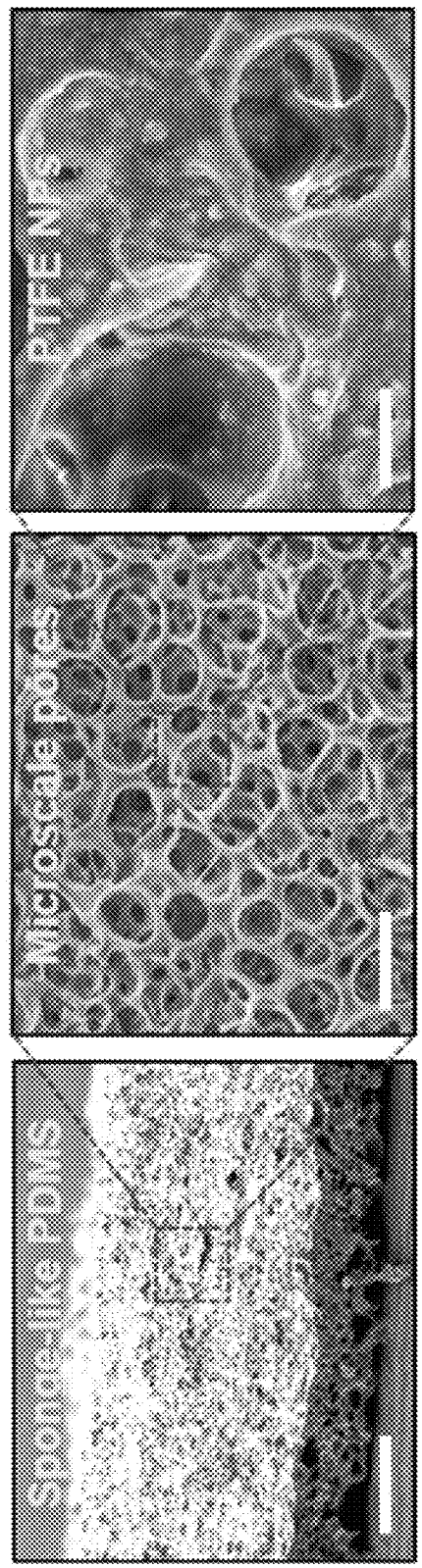

To promote and retain an ultra floatation capability, a sponge-like PDMS buoyant member is incorporated with polytetrafluorethylene (PTFE) nanoparticles (NPs, 0.2~5 μm dia.) covered by a thin layer of medical grade TEFLON® (AF2400, DuPont, USA), leading to substantial increase of the buoyancy force and the surface tension by greater than 20% and 35%, respectively (FIG. 1B). This ultra floatation capability allows the scaffolds to keep out of the cell culture medium even against intentional force up to about 51 N/m2 (FIG. 1C), while continuously offering favorable environments for both electronics and cells. A series of scanning electron microscope (SEM) images of a sponge-like PDMS buoyant member appear in FIG. 1D, highlighting the internal features. Characterizations of the sponge-like PDMS buoyant member in terms of effective specific weight, contact angle, dynamic droplet behavior, and critical immersion weight and depth appear in FIGS. 5A-5F, with the summarized results in Table S1 of FIG. 13. FIG. 12 presents experimental results showing that the electrical impedance of the scaffold system remained nearly unaffected when deployed on the surface of a cell medium in an incubator (Midi CO2 Incubators, Thermo Scientific, USA) at 37° C. under an atmosphere with 5% of CO2 over 2 weeks, whereas abrupt reduction of the impedance occurred within a short period of time in control groups without a microporous sponge-like buoyant member and with a conventional encapsulation using untreated (non-porous) PDMS due to short-circuit paths resulting from wetting and penetration by the cell media.

Figure 6:
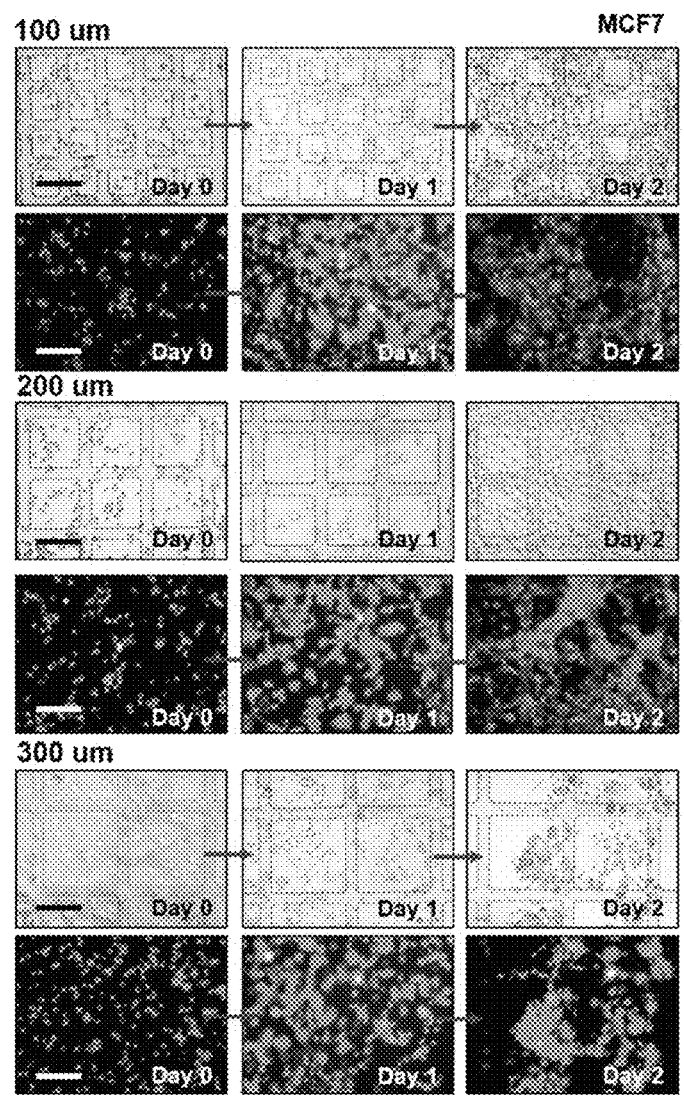
FIG. 6 includes DIC and confocal fluorescence microscope images of GPF-MCF7 cells seeded on the scaffold with the mesh pore size of 100 μm (top), 200 μm (middle) and 300 μm (bottom) (green=GFP). Scale bars are 200 μm.

Cell compatibility of the scaffold system is a key consideration for its implementations in 3D cell culture. FIG. 2A (red bars) presents representative results of a cell compatibility assay (MTT, Sigma-Aldrich, USA) for the scaffold seeded with green fluorescent protein (GFP)-expressed MCF7 cells and floated upside down on the medium. Prior to the cell seeding, the scaffold along with the sponge-like PDMS buoyant member was sterilized with 70% (v/v) ethanol for 30 min and dried under ultraviolet (UV) irradiation for 1 hour and then stored in an incubator at 37° C. under an atmosphere with 5% of $CO_2$. The results show that the proliferation rate of the cells increased consistently throughout the assay period (two days) while displaying no substantial difference compared to those obtained from a control group without any electronics embedded inside (black bars). FIG. 2B shows corresponding confocal fluorescence microscope images of a monolayer of the cells at day 2, wherein the yellow dash lines indicate the embedded recording electrodes (Au, 150 nm). The cells became confluent and started to cover the scaffold system when the size of the mesh holes was smaller than 200 μm. Non-uniform distribution of the cells appeared in the specimens that exhibit the mesh hole size of greater than 300 μm (FIG. 6). A control experiment on green immunofluorescence stained cardiomyocyte cells at the 8-day incubation produced consistent results (FIG. 2C), confirming that the scaffold system was conducive to cell growth, proliferation and extracellular matrix formation. Details about the cell culture and associated experimental procedures appear in the Methods section below.

Another aspect is that the scaffolds can be stacked multiple layers within a single matrix, providing desired 3D cell culture environments where cells can grow and interact with the surrounding in all dimensions to form tissues for a variety of tissue engineering applications. FIG. 2D presents an example of a four-layer stacked scaffold surrounded with dense cell (MCF7) layers after the 3-day incubation, with the corresponding confocal fluorescence microscope image in FIG. 2E. The results consistently indicated that the scaffold supports cell growth and tissue formation. Furthermore, alternative stacking of the scaffold seeded with specific sequence of different cells is possible, thereby yielding 3D hetero-cellular environments. FIGS. 2F and G show representative confocal fluorescence microscopy images for the scaffold with alternatively stacked cancer cells (i.e., GFP-MCF7) and endothelial cells (i.e., GFP-HUVEC cells). The cell layers were separately incubated for 2 days under different culture conditions, and then stained with DAPI and Draq5 for the MCF7 and HUVEC cells, respectively. The corresponding top view images in FIG. 7 highlight the confluent layers of well-attached cells with normal morphologies. The formation of vascular tubes in the HUVEC cells occurred, exhibiting extensive branches with typical lengths of 80 μm at day 3. The subsequent treatment of both vascular endothelial growth factor (VEGF) and fibroblast growth factor (β-FGF) remains required to form the tumor vasculature, thereby allowing for more systematic investigations.

Figure 8A:
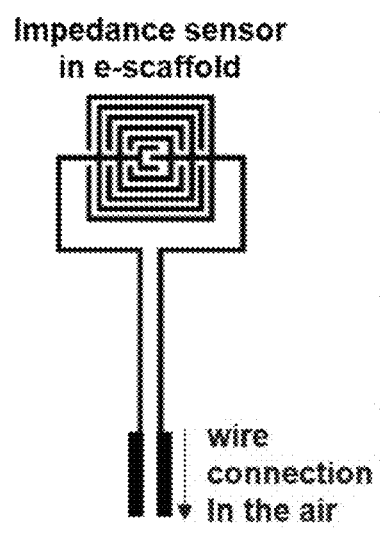
FIG. 8A includes a schematic representation of a nonlimiting embodiment of an impedance sensor embedded in a scaffold, and FIG. 8B includes SEM, DIC, and confocal fluorescence microscope images of the scaffold seeded with GFP-MCF7 cells at day 1 (green=GFP). Scale bars are 300 μm, 100 μm, 100 μm, and 100 μm from the top left, top right, bottom left, and bottom right.
Figure 8B:
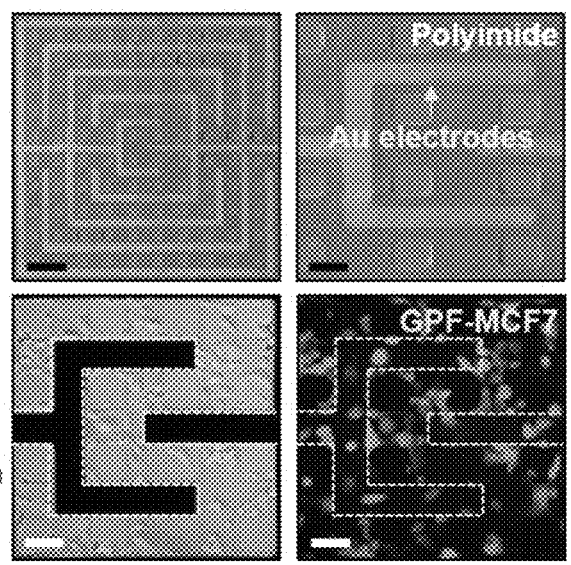
Figure 9A:
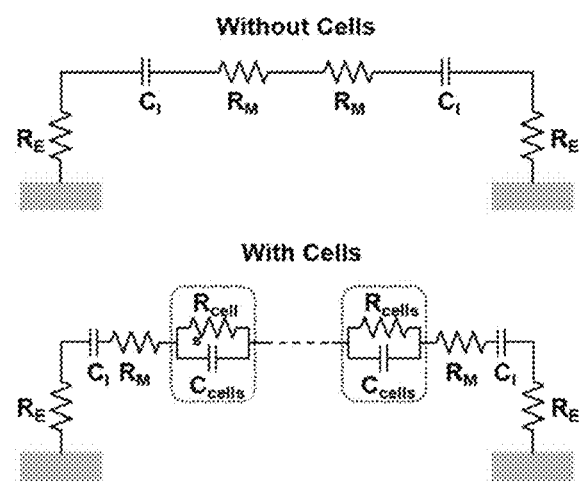
FIG. 9A includes equivalent circuits for an impedance sensor without (top) and with (bottom) cells.
Figure 9B:
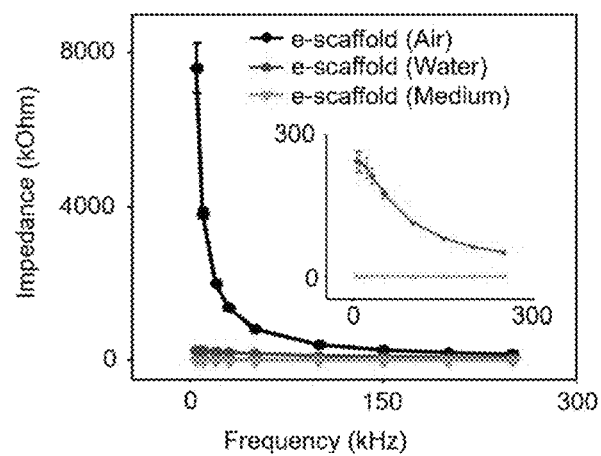
FIG. 9B is a measured frequency-impedance curve of the scaffold at the frequency range of 1-250 kHz.

Real-time monitoring of electrical cell-substrate impedance presents a non-labeling technique to understand cellular functions such as adhesion, growth, differentiation, mitigation and drug effect on cell behaviors. Biological cells serve as dielectric particles due to the insulating properties of their membranes, and therefore their attachment and detachment affect the current flow between the recording electrodes, leading to distinguishable changes in the impedance values. To illuminate this capability, a model system of the scaffold system was constructed into a configuration of interdigitated arrays (width: 80 μm, gap: 100 μm) of the embedded recording electrodes (Au, 150 nm) for the measurement of electrical impedance (FIGS. 8A and 8B). The equivalent circuit model appears in FIG. 9A, showing the recording electrode resistance ($R_E$), cell culture media ($R_{media}$), Helmholtz double layer interfacial capacitance ($C_I$), and additional resistance ($R_{cells}$) and capacitance ($C_{cells}$) by the introduction of cells. The recording electrodes act as a normal capacitor wherein the resulting impedance ($X_c=1/jwC$, $C=(\varepsilon_r\ \varepsilon_0 A)/d$) is subject to frequency (ω), dielectric constant ($\varepsilon_r$) of the surrounding materials (air=1.00059, water=80.4, medium=80), and cross sectional area of the recording electrode (A=about 3,900 μm$^2$) and gap between the interdigitated arrays (d=100 μm). A representative frequency-impedance curve of the scaffold at the frequency range of 1-250 kHz appears in FIG. 9B. Details about the measurement of cellular impedance appear in the Methods section below.

Figure 10:
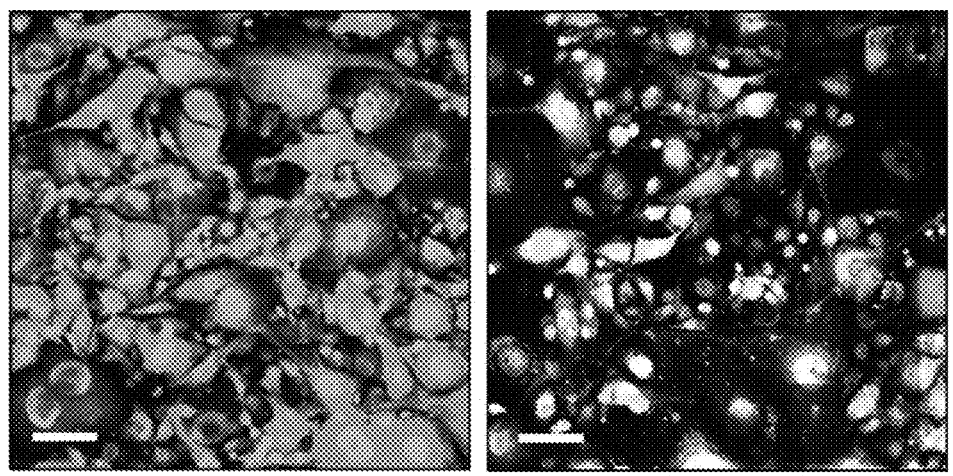
FIG. 10 includes confocal fluorescence microscope images of the GFP-MCF7 cells without (left) and with (right) the administration of Dox (1 mM) (green=GFP, red=Draq5 and blue=DAPI). Scale bars are 100 μm.

FIG. 3A shows a representative SEM (left), microscopy (middle), and conformal microcopy (right) images of the model scaffold system within a Matrigel™ seeded with MCF7 cells after 1 hour of incubation. The scaffold system remained afloat on the medium, wherein the recording electrodes were entirely surrounded with polyimide elastomers. The flexible conductors were ACF cables (HST-9805-210, Elform, Inc., USA) placed on the sponge-like PDMS buoyant member and wired to an external data acquisition system (E4980AL Precision LCR meter, Keysight Technologies, USA) through the air. FIG. 3B shows the results of time-dependent impedance obtained separately from MCF7 cells (black line), SKOV3 cells (red line), and HUVEC cells (green line) for 50 hours during the period of growth and proliferation. The results show that the impedance increased linearly for first about 4 hours when the cells started to settle down and become adherent to the recording electrodes, implying that the cells acted as an electrical insulating medium. From about 16 hours later, drastic increase of the impedance occurred due to the cell aggregation and continuous proliferation. This tendency was more obvious in the MCF7 cells because the population doubling time of MCF7 cells (about 29 hours) is shorter than that of SKOV3 cells (about 48 hours) and HUVEC cells (about 60 hours). Consistently, the impedance of the MCF7 cells increased proportionally to the cellular density (FIG. 3C). An impedimetric cytotoxicity plot for the MCF7 cells appears in FIG. 3D, while a model drug, such as a hydrophilic and water-soluble doxorubicin (Dox, Doxorubicin Hydrochloride, Fisher, USA; solubility about 50 mg/ml), was introduced in the medium with different dosages at the 1-day incubation. The results reveal that the impedance started to decrease within about 4 hours after the drug administration (100 µM) when the effect of the Dox becomes apparent and eventually leads to the cell death and detachment (FIG. 10). It was observed that no substantial decrease of the impedance appeared in the control specimens with the low drug administration (10 µM).

Stacking multiple layers of scaffolds provides the capability to monitor spatially-resolved impedance from cultured cells in 3D structured environments that can more closely resemble in vivo tissue environments. FIG. 3E shows a schematic illustration for the three-layer stacked scaffold within a single Matrigel™ seeded with MCF7 cells, which is floated upside down on the medium by using the sponge-like PDMS buoyant member. In this configuration, each layer of the scaffold system remains spaced apart a fixed distance of about 5 mm along the perimeter by using spacers made of PDMS. FIG. 3F shows the time-dependent impedance obtained from each layer of the scaffold system on the top (black line), middle (red line), and bottom (green line), while 1 mM of Dox was introduced on the top at the 1-day incubation. The impedance increased at nearly the same rate during the cell growth and proliferation, and then abruptly decreases following the drug administration with different rates (top: about 10.1 Ω/hr, middle: about 5.4 Ω/hr, bottom: about 1.6 Ω/hr), as the Dox molecules diffused downward from the top. These results were consistent with the confocal fluorescence microscopy images obtained from the top, middle, and bottom layer of the scaffold system at 12 hours after the treatment of Dox (1 mM), indicating that the top layer contained the most Dox, followed by the middle and bottom layers. This platform for the real-time impedimetric analysis of drug-induced cellular events in 3D culture environments can provide important insights into the mechanism of complex cellular phenomena for the identification of diseased cells at different stages and their interactions with therapeutic agents.

Figure 11A:
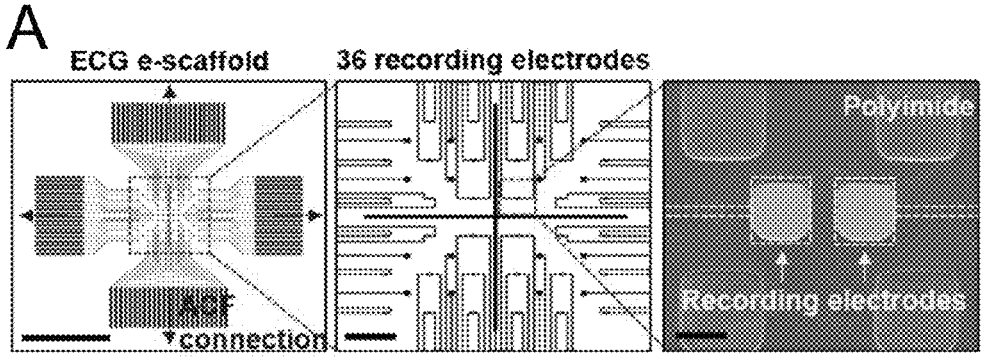
FIG. 11A includes schematic representations and an SEM image of an scaffold embedded with 36 ECG recording electrodes. Scale bars are 1 cm, 100 μm, and 40 μm from the left, FIG. 11B includes confocal fluorescence microscope images of the cardiomyocytes stained with sarcomeric α-actinin on the scaffold (green=FITC, red=Draq5). Scale bars are 20 μm, 10 μm, and 10 μm from the left.
Figure 11B:
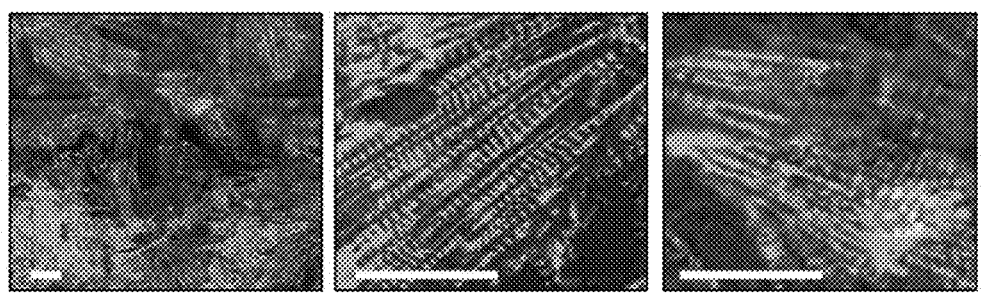

Real-time 3D monitoring of electrical impedance and/or electrophysiological signals in electrically active cells such as the heart, brain and muscle cells enables spatially-resolved quantitative analysis of action potential propagations to understand tissue development, drug modulation and functions of diseased or damaged tissues. To demonstrate the potential use of the scaffold system in this context, a model system of the three-layer stacked scaffold system was constructed within a single Matrigel™ containing cardiomyocytes and tailored for the detection of electrocardiography (ECG) signals. Each layer of the scaffold system consisted of 36 recording electrodes (Au, 150 nm, width=60×60 µm$^2$, electrode gap=10 µm, distance between the recording electrodes=1,150 µm) (FIG. 11A).). In this configuration, the monitoring of the cellular contractions occurs on each recording electrode while the array-type mapping reveals the spatial distributions and variations of the cardiomyocyte throughout the 3D environment. The cardiomyocyte underwent maturation in culture, leading to formation of a tissue layer aligned to the scaffold system at day 8 in vitro (FIG. 11B). The representative immunostained confocal images of cardiomyocytes stained with sarcomeric α-actinin taken from several different areas after 8 days of the incubation reveal that cardiomyocytes are homogeneously distributed along the surface and elongated with high aspect ratios, providing information on the maturation of cells and formation of tissues with hallmarks of the native myocardium. As the cardiomyocytes mature, the sarcomeres assemble in series to form myofibrils that extend across the cells wherein the myofibrils are anchored to the ends of the cardiomyocytes by the cell-cell junctional structure.

Figure 4A:
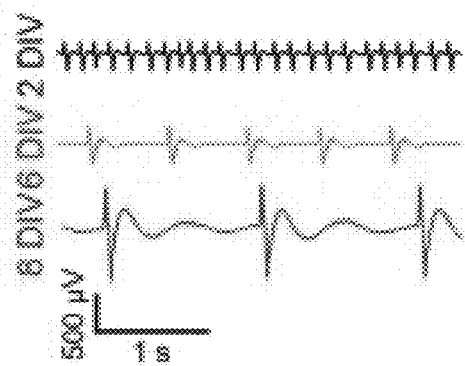
FIGS. 4A-4E represent 3D mapping of cardiac action potential.
Figure 4B:
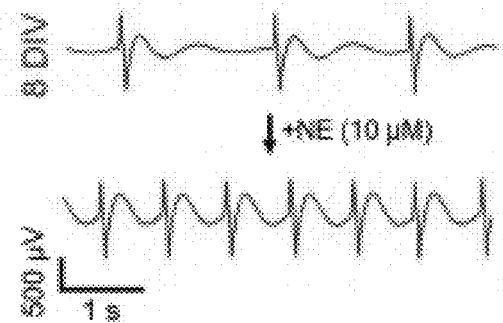
Figure 4C:
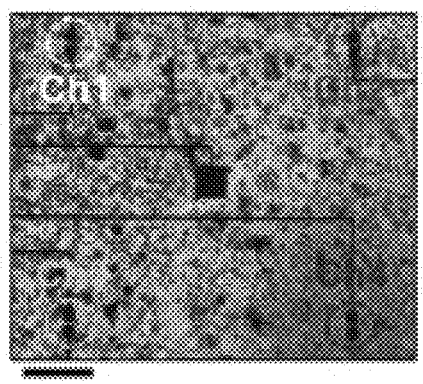
Figure 4D:
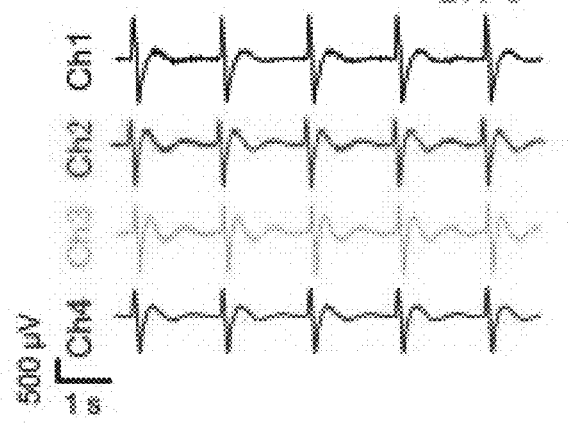
Figure 4E:
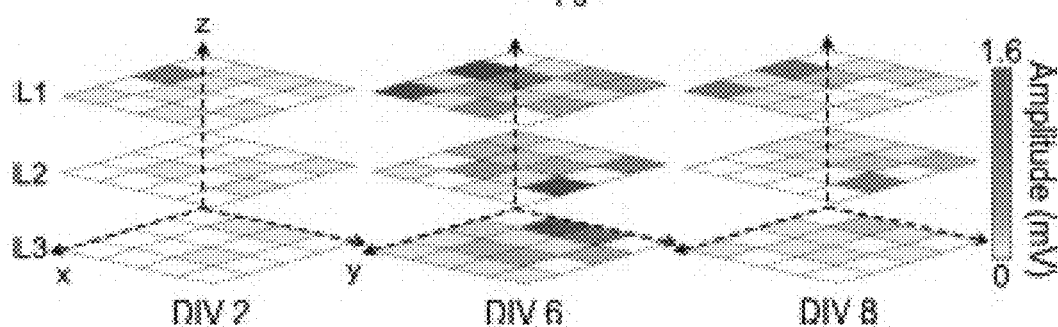
Figure 5A:
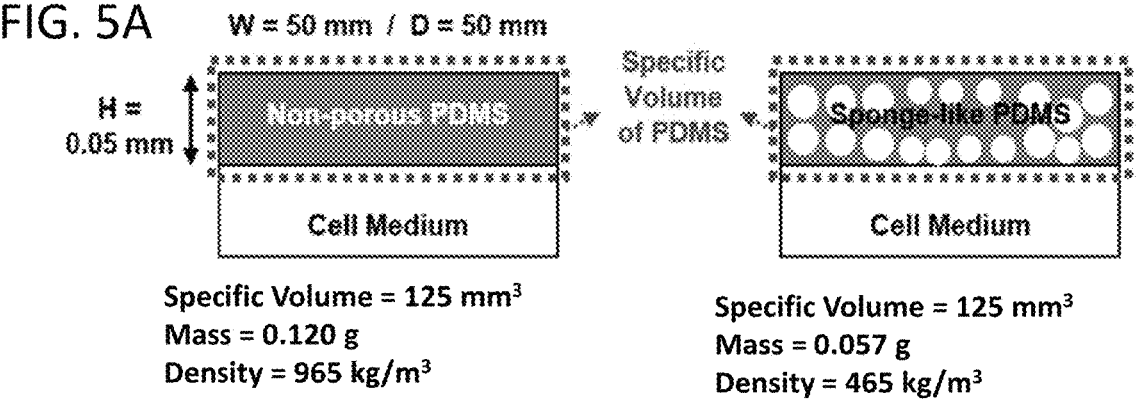
FIGS. 5A-5F include images representing a summary of the measured surface tension (FIG. 5A), static contact angle (FIGS. 5B and 5C), dynamic droplet (FIG. 5D), and critical immersion weight and depth (FIGS. 5E and 5F) for the sponge-like PDMS buoyant member. Scale bars are 2.5 mm and 1 cm.
Figure 5B:
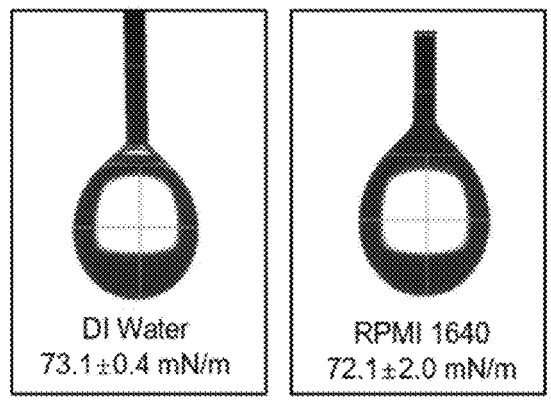
Figure 5C:
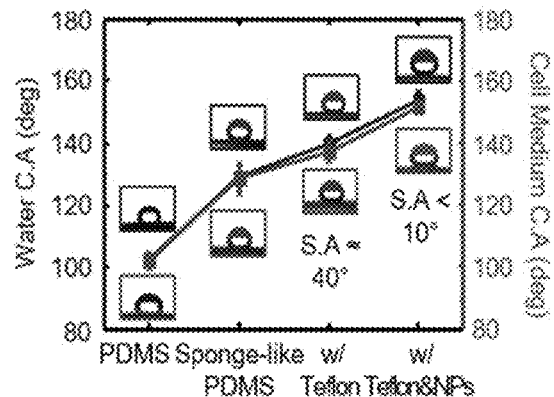
Figure 5D:
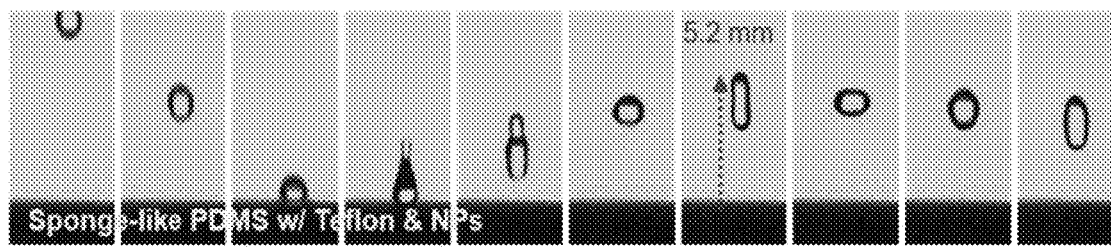
Figure 5E:
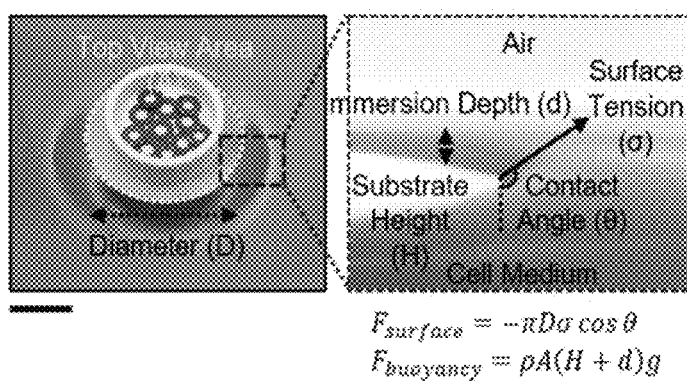
Figure 5F:
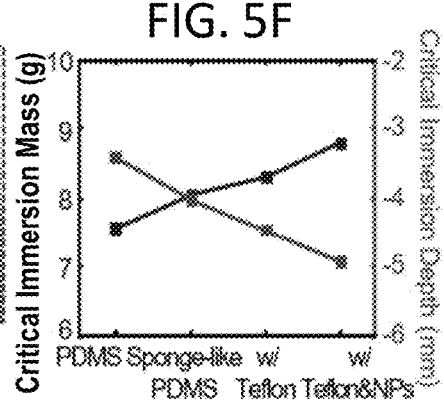

FIG. 4A shows recorded ECG signals in real time from the cardiomyocytes at day 2, 6, and 8, exhibiting typical shape of cardiac action potential signals at the frequency of 4.8, 1.0, and 0.6 Hz, respectively. The beating rate decreased from 288 bpm to 60 bpm and to 36 bpm, whereas the amplitude increased from 66 µV to 83 µV and to 511 µV at day 2, 6, and 8, respectively. The results imply that spontaneous contractions of the individual cells initially occurred, followed by stronger and more synchronized contractions as the cells become more in contact each other. FIG. 4B shows continuously recorded ECG signals from the cardiomyocytes at day 8 in response to the addition of 100 µL of norepinephrine (NE) into the medium, displaying that the beating rate increases nearly two-fold within about 3 min after the NE administration. A representative microscopy image in FIG. 4C highlights the embedded four-channel-multiplexed sensing electrodes with the cardiomyocytes at day 8 within the domain of 1.4×1.4 mm$^2$. The results in FIG. 4D indicate the synchronized beating rate (about 0.63 Hz), amplitude (638~763 µV), and peak width (~about 0.6 sec). 3D mapping results of the action potentials (FIG. 4E) obtained from the total 48 ECG sensors (4×4 array in each layer) reveal the spontaneous beating activities of the cardiomyocytes at day 2, 6, and 8 without showing any toxic effect. The analysis consistently showed that the cellular contractions expanded spontaneously in all dimensions throughout the 3D environments.

The results obtained from the above-described investigations demonstrated that a scaffold system integrated with an engineered ultra-buoyant member on a culturing medium allows long-term, real-time monitoring of cellular behaviors and functions in favorable environments for both electronics and cells. The physical stacking of the scaffolds enables the incorporation of large numbers of addressable sensors in a multi-directional arrangement, offering the 3D mapping capability. These findings suggest an expanded set of potential options such as long-term stable monitoring of tissue functions during/after in vivo transplant to replace diseased or damaged tissues. The real-time monitoring of cellular behaviors and functions with temporal resolutions during endothelial lumen formation in tumor tissue or during the invasion of SKOV3 cells into HUVEC cells to obtain information on their interactions between invading cancer cells and the adherent cells would be highly desired, suggesting directions for future research. In addition, it is foreseeable and within the scope of the invention that the scaffold system may be constructed with a bioresorbable form such that the whole constituent materials degrade harmlessly in the body following implantation and after a clinically useful period, thereby eliminating the need for post-surgical extraction. Furthermore, although the teachings disclosed herein focus on the advantages provided by impedance and electrophysiology sensors, the systems may be instrumented with more diverse sensing modalities, such as but not limited to detect pH, pressure, temperature and/or mechanical strains.

Materials and Methods

The fabrication of the scaffold system began by spin-casting the layers of PMMA (1 µm thick) and polyimide (1 µm thick) on a Si substrate. Thin films of Cr/Au film (5 nm/150 nm) were deposited by using an electron-beam (e-beam) evaporator. A photolithographic patterning with a photoresist (AZ 1518, 3,000 rpm, 30 s) and subsequent wet etching steps in solutions of Cr and Au etchants (Transene, Inc.) followed to define the metallic thin film electrodes and the interconnecting traces. The encapsulation layer of polyimide (1 µm thick) was spin-casted on top and patterned by photolithography with a photoresist (AZ 9260, 3,000 rpm, 1 min) and oxygen ($O_2$) plasma reactive ion etching (RIE) to define the basic structure of the scaffold system.

The fabrication of a sponge-like PDMS buoyant member began by spin casting a mixture of PDMS base material and curing agent (10:1 weight ratio) on a glass substrate at 100 rpm for 10 min. The as prepared PDMS was then placed into a pressure cooker maintained at the pre set pressure (90 kPa) and temperature (100° C.) for 20 min. The microscale pores were formed during the high pressure steaming step while the PDMS was completely polymerized, providing for superhydrophobicity and an anti-wetting performance. The resulting microporous sponge-like PDMS buoyant member was dried in a convection oven at 70° C. for 1 hour to remove the residual water molecules. A solution of TEFLON® (1 wt % AF2400, Dupont, USA) mixed with PTFE nano particles (0.2 5 µm, Polysciences, Inc. and Sigma Aldrich, USA) was spin casted at 1,000 rpm for 5 min, and then cured at 150° C. on a hot plate to increase the surface tension force, leading to an increased static water contact angle and a decreased effective surface adhesion against a cell medium.

The static contact angle was measured by placing a droplet (about 10 µL) of distilled (DI) water and oil on a specimen by using a computer-controlled contact angle analyzer (Surface Electro Optics, Phoenix-10). The dynamic droplet behaviors of DI water and oil when dropped (about 154) from a height of about 4 cm were monitored by using a high speed camera at 50 frames per second.

The buoyancy force was measured by adding equally balanced weights (about 0.25 g) one after another on the top surface of a specimen afloat on the culture medium (RPMI1640, Sigma-Aldrich, USA). The total supporting buoyancy force was estimated according to the critical weight by which the specimen was immersed.

The specimens of the cell compatibility assay were sterilized by soaking in 70% (v/v) ethanol for 30 min and rinsing twice with phosphate buffer saline (PBS), followed by dehydration under UV irradiation for 1 hr. The specimens were treated with 02 plasma (35 W, 3 min) and immersed in fibronectin/gelatin solution (0.5% fibronectin, F1141, Sigma-Aldrich, USA and 0.02% gelatin, Fisher Scientific, USA) for 1 day. The cells suspended in 50% medium and 50% Matrigel™ (Corning Life Sciences, USA) were then seeded on the specimens. In order to assess the cell proliferation, about $5 \times 10^3$ cells were seeded and incubated. After the incubation, 3-(4,5-dimethylthiazol-2-yl)-2,5-diphenyltetrazolium bromide (MTT, Sigma-Aldrich, USA) was treated to the cells, and the fluorescent intensity was measured at 580 nm by using a microplate reader (SpectraMax Plus 384 reader, Molecular Devices, USA). For the confocal microscopy analysis, the cells were fixed with 4% v:v paraformaldehyde in PBS for 15 min, stained with DAPI (500 nM, Invitrogen, USA) or Draq5 (1 µM, Invitrogen, USA) for 2 min and mounted with an antifade reagent. The resulting cells were imaged by using the A1Rsi confocal microscope (Nikon, Japan).

For cardiomyocyte isolation, primary neonatal mice cardiomyocytes were prepared according to the Pierce Primary Cardiomyocyte Isolation Kit (Thermo Scientific, USA). Briefly, neonatal hearts were isolated from about 1 to 3 days old neonatal mice and placed into separate sterile microcentrifuge tubes containing 500 µL of ice cold Hank's Balanced Salt Solution (HBSS). Each isolated heart was then minced into about 1 to 3 $mm^3$ pieces and washed twice with 500 µL of ice cold HBSS to remove blood from the tissue. The minced tissues were incubated with 200 µL of reconstituted Cardiomyocyte Isolation Enzyme 1 (with papain) and 10 µL of Cardiomyocyte Isolation Enzyme 2 (with thermolysin) to each tube in an incubator at 37° C. for 30 min. After the incubation, the tissues were removed from the enzyme solution and washed twice with 500 µL of the ice cold HBSS and added 500 µL of complete Dulbecco's modified Eagle's medium (DMEM) for primary cell isolation to the tissues. The cardiomyocytes ($6 \times 10^6$) were seeded onto a specimen with 50% medium and 50% Matrigel™ (Corning Life Sciences, USA). The cell constructs were supplemented with complete DMEM for primary cell isolation and further incubated.

For the cardiomyocyte immunostaining, the cardiomyocytes were fixed with 4% paraformaldehyde (Electron Microscope Sciences, USA) in PBS for 30 min and then washed three times with PBS. The cardiomyocytes were incubated with 0.25% Triton X-100 (Sigma-Aldrich, USA) in PBS for 1 hour, and washed three times with ice-cold PBS and pre-blocked for 1 hour at room temperature in PBS containing 10% FBS, after which the specimens were washed three times with PBS. The specimens were incubated with primary anti-sarcomeric α-actinin mouse monoclonal antibodies (1:250; Sigma-Aldrich, USA) in SuperBlock™ (TBS) Blocking Buffer solution (Thermo Scientific, USA) for 1 hour at room temperature, and washed three times and then incubated with AlexaFluor-488 goat anti-mouse secondary antibody (1:400; Invitrogen, USA) for 1 hour, followed by rinsing with PBS. For the cell nuclei staining, the cardiomyocytes were stained with 1 µM of Draq5 for 2 min and then rinsed with PBS. The resulting specimens were imaged by using the A1Rsi confocal microscope (Nikon, Japan).

The impedance was measured by using an LCR meter (Agilent 4294A, USA) with the voltage (between two adjacent recording electrodes) of about 1 mV for 48 hours at the frequencies of 1, 5, 10, 20, 30, 50, 100, 150, 200 and 250 kHz. The scaffold system was placed in the incubator (5% $CO^2$, 37° C.; Thermo Scientific, USA) and wired to the LCR meter located outside of the incubator via flexible ACF cables. The data was collected every 2 hours from the scaffold system. The frequency responses of the cytotoxic effects were obtained by measuring the impedance of the MCF7 cells treated with different doses of Dox at the frequency of 30 kHz.

The ECG signals of the cardiomyocytes were acquired by using the multichannel electrophysiological data acquisition unit (BioRadio™, USA) with the notch filter (60 Hz) and the custom filter (Filter type: Bandpass, Filter design: Butterworth, Order: 4, Lower cutoff: 0.5, Upper cutoff: 10). The scaffold system was placed in the incubator (5% $CO^2$, 37° C.; Thermo Scientific, USA) and wired to the data acquisition unit via flexible ACF cables. The data was collected at the sample rate of 2 kHz through differential programmable channels, and then post-processed by using a commercial software (BioCapture). The solution of norepinephrine bitartrate (10 µM; Sigma-Aldrich, USA) was used to increase the cardiomyocyte beating rate.

While the invention has been described in terms of specific or particular embodiments and investigations, it should be apparent that alternatives could be adopted by one skilled in the art. For example, the system and its components could differ in appearance and construction from the embodiments described herein or shown in the drawings, functions of certain components of the system could be performed by components of different construction but capable of a similar (though not necessarily equivalent) function, process parameters could be modified, and appropriate materials could be substituted for those noted. As such, it should be understood that the above detailed description is intended to describe the particular embodiments, including those represented in the drawings, and certain but not necessarily all features and aspects thereof, and to identify certain but not necessarily all alternatives to the embodiments and described features and aspects thereof. As a nonlimiting example, the invention encompasses additional or alternative embodiments in which one or more features or aspects of a particular embodiment could be eliminated or two or more features or aspects of different embodiments could be combined. Accordingly, it should be understood that the invention is not necessarily limited to any embodiment described herein or illustrated in the drawings, and that the purpose of the above detailed description and the phraseology and terminology employed therein is to describe the disclosed embodiments and investigations and not necessarily to serve as limitations to the scope of the invention. Therefore, the scope of the invention is to be limited only by the following claims.

The invention claimed is:

1. A buoyant instrumented tissue scaffold system for sensing behaviors and/or functions of cells or tissues in a culturing medium, the system comprising:
a buoyant member comprising a sheet of hydrophobic microporous polydimethylsiloxane (PDMS) coated with a surface tension increasing covering, the sheet having an opening through a central portion thereof;
a scaffold supported on the buoyant member and disposed in the opening, the buoyant member being anchored to a peripheral area of the scaffold, the scaffold comprising one or more flexible members and one or more sensor arrays on the one or more flexible members, the one or more sensor arrays being configured to sense the behaviors and/or functions of the cells or tissues in the culturing medium; and
a transmitting means functionally coupled to the one or more sensor arrays for transmitting information obtained thereby to an external data acquisition unit;
wherein the buoyant member maintains the scaffold and the transmitting means afloat on a surface of the culturing medium, enables the cells or tissues to reside and grow beneath the scaffold, and is a barrier to wetting of the one or more sensor arrays by the culturing medium.

2. The buoyant instrumented tissue scaffold system of claim 1, wherein the system comprises a plurality of the scaffold in a stacked configuration, and each of the scaffolds comprises one or more of the one or more sensor arrays on one or more of the flexible members.

3. The buoyant instrumented tissue scaffold system of claim 2, the system further comprises means for producing a three dimensional (3D) map based on information received from the one or more sensor arrays.

4. The buoyant instrumented tissue scaffold system of claim 1, wherein the behaviors and/or functions of the cells or tissues sensed by the one or more sensor arrays comprise at least one of cellular electrical impedance and cellular electrophysiological signals of the cells or tissues.

5. The buoyant instrumented tissue scaffold system of claim 1, wherein at least one sensor of the one or more sensor arrays senses pH, pressure, temperature, and/or mechanical strains.

6. The buoyant instrumented tissue scaffold system of claim 1, wherein the culturing medium is a cell culture medium.

7. The buoyant instrumented tissue scaffold system of claim 1, wherein the culturing medium is an in vivo tissue environment.

8. The buoyant instrumented tissue scaffold system of claim 1, wherein the scaffold comprises a waterproof encapsulation layer that encases the one or more sensor arrays.

9. The buoyant instrumented tissue scaffold system of claim 1, wherein the transmitting means comprises flexible conductors connecting the one or more sensor arrays with the external data acquisition unit.

10. The buoyant instrumented tissue scaffold system of claim 1, wherein the buoyant member is a microporous water-repellent film and the surface tension increasing covering comprises polytetrafluorethylene nanoparticles mixed with polytetrafluorethylene.

11. The buoyant instrumented tissue scaffold system of claim 1, wherein the scaffold comprises thin film electrodes disposed on a first layer of polyimide and encapsulated with a second layer of polyimide.

12. The buoyant instrumented tissue scaffold system of claim 1, wherein the one or more flexible members encapsulate the one or more sensor arrays.

13. The buoyant instrumented tissue scaffold system of claim 12, wherein the one or more flexible members are formed of an elastomeric polyimide.

14. The buoyant instrumented tissue scaffold system of claim 1, wherein the culturing medium surrounds the scaffold.

15. A method of sensing behaviors and/or functions of cells or tissues in a culturing medium using the buoyant instrumented tissue scaffold system of claim 1, the method comprising:
locating the scaffold on the culturing medium such that the buoyant member floats on or in the culturing medium and is a barrier to wetting of the sensor arrays by the culturing medium;
allowing the cells or tissues to reside and/or grow beneath the scaffold;
detecting the behaviors and/or functions of the cells or tissues with the sensor arrays; and
transmitting data to the external data acquisition unit corresponding to the behaviors and/or functions.

16. The method of claim 15, wherein the behaviors and/or functions of the cells or tissues sensed by the sensor arrays comprise at least one of cellular electrical impedance and cellular electrophysiological signals of the cells or tissue.

17. The method of claim 15, wherein at least one sensor of the sensor arrays senses pH, pressure, temperature, and/or mechanical strains.

18. The method of claim 15, wherein the culturing medium is a cell culture medium.

19. The method of claim 15, wherein the culturing medium is an in vivo tissue environment.

20. The method of claim 15, further comprising producing a three-dimensional (3D) map based on the behaviors and/or functions of the cells or tissues.

\* \* \* \* \*